United States Patent
Zinke et al.

(10) Patent No.: US 6,169,111 B1
(45) Date of Patent: Jan. 2, 2001

(54) CONFORMATIONALLY RIGID ARYL PROSTAGLANDINS FOR USE IN GLAUCOMA THERAPY

(75) Inventors: Paul W. Zinke, Fort Worth, TX (US); John E. Bishop, Groton, MA (US); Thomas R. Dean, Weatherford; Mark R. Hellberg, Arlington, both of TX (US)

(73) Assignee: Alcon Laboratories, Inc., Fort Worth, TX (US)

(*) Notice: Under 35 U.S.C. 154(b), the term of this patent shall be extended for 0 days.

(21) Appl. No.: 09/308,052

(22) PCT Filed: Nov. 12, 1996

(86) PCT No.: PCT/US96/17901

§ 371 Date: May 12, 1999

§ 102(e) Date: May 12, 1999

(87) PCT Pub. No.: WO98/21180

PCT Pub. Date: May 22, 1998

Related U.S. Application Data

(63) Continuation-in-part of application No. 08/480,707, filed on Jun. 7, 1995, now Pat. No. 5,698,733.

(51) Int. Cl.$^7$ .................................................. A61K 31/557
(52) U.S. Cl. .......................... 514/530; 514/443; 514/469; 514/569; 514/621; 514/622; 514/657; 514/681; 514/682; 514/719; 514/729
(58) Field of Search .................................... 514/530, 443, 514/469, 569, 621, 622, 657, 681, 682, 719, 729

(56) References Cited

U.S. PATENT DOCUMENTS

| | | |
|---|---|---|
| 4,004,021 | 1/1977 | Bowler et al. ........................ 514/530 |
| 4,152,527 | 5/1979 | Hess et al. ............................ 562/462 |
| 4,321,275 | 3/1982 | Bowler et al. ........................ 562/462 |
| 5,093,329 | 3/1992 | Woodward ............................ 514/469 |
| 5,151,444 | 9/1992 | Ueno et al. ............................ 514/530 |
| 5,302,617 | 4/1994 | Ueno .................................... 514/573 |
| 5,321,128 | 6/1994 | Stjernschantz et al. .............. 514/530 |
| 5,422,368 | 6/1995 | Stjernschantz et al. .............. 514/530 |
| 5,446,041 | 8/1995 | Chan et al. ........................... 514/530 |
| 5,741,810 * | 4/1998 | Burk .................................... 514/530 |
| 5,834,498 * | 11/1998 | Burk .................................... 514/445 |

FOREIGN PATENT DOCUMENTS

| | | |
|---|---|---|
| 0330511 A2 | 8/1989 | (EP) . |
| 0435682 A2 | 7/1991 | (EP) . |
| 0561073 A1 | 9/1993 | (EP) . |
| 0603800 A1 | 6/1994 | (EP) . |
| 0667160 A2 | 8/1995 | (EP) . |
| 1539268 | 1/1979 | (GB) . |
| WO 92/02496 | 2/1992 | (WO) . |
| WO 92/08465 | 5/1992 | (WO) . |
| WO 94/06432 | 3/1994 | (WO) . |
| WO 94/08587 | 4/1994 | (WO) . |
| WO 96/10407 | 4/1996 | (WO) . |
| WO 96/36599 | 11/1996 | (WO) . |

OTHER PUBLICATIONS

Braun, et al.,*Effect of ZK 110.841 on Cerebral Vascular Contraction and $TXA_2$–Release Caused by Thrombin–Stimulated Platelets*, Archives of Pharmacology 339 Suppl:R37, No. 148 (1989).

Hayashi et al.,*Prostaglandin Analogues Possessing Antinidatory Effects. I. Modification of the ω Chain*,J. Med. Chem. 23(5):519–524 (1980).

Ney, Potent Inhibition of FMLP–Induced Neutrophil Activation by the $PGD_2$ Analogue ZK 110.841, Archives of Pharmacology, 339 Suppl:R38, No. 150 (1989).

New Research Drug DLO/8149, Drug License Opportunities (IMSWORLD Publications) (Jun. 25, 1990).

Schaaf et al., Structure–Activity Studies of Configurationally Rigid Arylprostaglandins, *J. Med. Chem.* 26(3):328–334 (1983).

* cited by examiner

*Primary Examiner*—Bernard Dentz
(74) *Attorney, Agent, or Firm*—Barry L. Copeland

(57) ABSTRACT

Conformationally rigid aryl prostaglandins are useful in the treatment of glaucoma and ocular hypertension. Also disclosed are ophthalmic pharmaceutical compositions comprising said prostaglandins.

11 Claims, No Drawings

CONFORMATIONALLY RIGID ARYL PROSTAGLANDINS FOR USE IN GLAUCOMA THERAPY

This application is a 371 of PCT/US96/17901 filed Nov. 12, 1996 which is a CIP of 08/480,707 filed Jun. 7, 1995 now U.S. Pat. No. 5,698,733.

BACKGROUND OF THE INVENTION

The present invention relates to the use of prostaglandins and prostaglandin analogues for the treatment of glaucoma and ocular hypertension. As used herein, the terms "prostaglandin" and "PG" shall refer to prostaglandins and derivatives and analogues thereof, except as otherwise indicated by context.

Naturally-occurring prostaglandins, especially prostaglandins of the F series (such as $PGF_{2\alpha}$ and the E series (such as $PGE_2$), are known to lower intraocular pressure (IOP) after topical ocular instillation, but can cause conjunctival hyperemia and/or edema as well as inflammation. Many synthetic prostaglandins have been observed to lower intraocular pressure, but most such compounds also produce the aforementioned side effects which significantly limit their clinical utility.

Various attempts have been made to overcome these well-known side-effects. Some have synthesized derivatives of naturally-occurring prostaglandins in an attempt to design out selectively the side effects while maintaining the IOP-lowering effect. See, e.g., Stjernschantz et al. (U.S. Pat. Nos. 5,422,368 and 5,321,128), Woodward et al. (U.S. Pat. No. 5,093,329), Chan et al. (WO 92/08465 and U.S. Pat. No. 5,446,041). Others, including Ueno et al. (EP 330 511 A2) and Wheeler (EP 435 682 A2) have tried complexing prostaglandins with various cyclodextrins.

SUMMARY OF THE INVENTION

It has now been unexpectedly discovered that certain conformationally rigid analogues of $PGF_{2\alpha}$ will lower or control IOP with no or significantly reduced side effects of conjunctival hyperemia and/or edema. An agent which exhibits comparable efficacy, but with reduced side effects when compared to other agents, is said to have an improved therapeutic profile.

While bound by no theories, it is believed that increased conformational rigidity resulting from the presence of a bicyclic ring at the terminus of the omega chain of the prostaglandins of the present invention allows increased discrimination amongst the various PG receptors, which, in turn, allows a higher separation of desirable and undesirable activities, and therefore an improved therapeutic profile.

DETAILED DESCRIPTION OF THE INVENTION

The conformationally rigid aryl prostaglandins which are useful in the compositions of the present invention have the general formula (I):

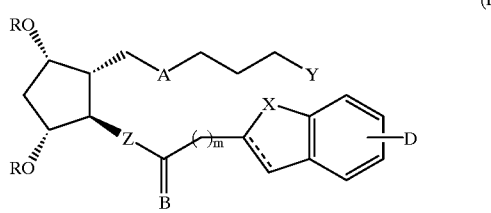

wherein:
Y=$C(O)NR_1R_2$, $CH_2OR_3$, $CH_2NR_1R_2$, $CO_2R_1$, $CO_2M$, where M is a cationic salt moiety;
$R_1$, $R_2$ (same or different)=H, $C_1$–$C_6$ alkyl or alkenyl, or $C_3$–$C_6$ cycloalkyl;
R, $R_3$ (same or different)=$C(O)R_4$, or H, where $R_4$=$C_1$–$C_6$ alkyl or alkenyl, or $C_3$–$C_6$ cycloalkyl;
A=$CH_2CH_2$, cis or trans CH=CH, or C≡C;
Z=$CH_2CH_2$, trans CH=CH;
X=O, $S(O)_n$, $(CH_2)_n$, or $CH_2O$, where n=0, 1, or 2;
B=H and OH in either configuration, or a double bonded O;
D=$R_1$, $OR_1$, halogen, $S(O)_nR_4$, $NO_2$, $NR_1R_2$, or $CF_3$, where n=0, 1, or 2, and $R_1$, $R_2$, and $R_4$ are as defined above; and
m=0, 1, or 2.

Most preferred compounds include:
II. (5Z, 13E)-(9S, 11R, 15S)-15-(2-indanyl)-9, 11, 15-trihydroxy-16, 17, 18, 19, 20-pentanor-5, 13-prostadienoic acid isopropyl ester.
III. (5Z)-(9S, 11R, 15R)-15-(2-indanyl)-9, 11, 15-trihydroxy-16, 17, 18, 19, 20-pentanor-5-prostenoic acid isopropyl ester.
IV. (5Z, 13E)-(9S, 11R, 15S)-15-(2R-(1,2,3,4-tetrahydronaphthyl))-trihydroxy-16, 17, 18, 19, 20-pentanor-5, 13-prostadienoic acid isopropyl ester.
V. (5Z, 13E)-(9S, 11R, 15S)-15-(2S-(1,2,3,4-tetrahydronaphthyl))-9, 11, 15-trihydroxy-16, 17, 18, 19, 20-pentanor-5, 13-prostadienoic acid isopropyl ester.
VI. (5Z, 13E)-(9S, 11R, 15R)-15-(2-benzo[b]furyl)-9, 11, 15-trihydroxy-16, 17, 18, 19, 20-pentanor-5, 13-prostadienoic acid isopropyl ester.
VII. (5Z, 13E)-(9S, 11R, 15R)-15-(2R-(2,3-dihydrobenzo[b]furyl)-9, 11, 15-trihydroxy-16, 17, 18, 19, 20-pentanor-5, 13-prostadienoic acid isopropyl ester.
VIII. (5Z, 13E)-(9S, 11R, 15R)-15-(2S-(2,3-dihydrobenzo[b]furyl)-9, 11, 15-trihydroxy-16, 17, 18, 19, 20-pentanor-5, 13-prostadienoic acid isopropyl ester.
IX. (5Z, 13E)-(9R, 11R, 15R)-15-(2R-[3,4-dihydro-2H-benzo[1,2-b]pyran-2-yl)-9, 11, 15-trihydroxy-16, 17, 18, 19, 20-pentanor-5, 13-prostadienoic acid isopropyl ester.
X. (5Z, 13E)-(9S, 11R, 15R)-15-(2S-3,4-dihydro-2H-benzo[1,2-b]pyran-2-yl)-9, 11, 15-trihydroxy-16, 17, 18, 19, 20-pentanor-5,13-prostadienoic acid isopropyl ester.

Some of the above-mentioned prostaglandins are disclosed in U.S. Pat. No. 4,152,527 (Hess et al.) issued on May 1, 1979, and in Hyashi, M., et al., *J. Med. Chem.* 23:519 (1980). To the extent that U.S. Pat. No. 4,152,527 discloses the synthesis of the prostaglandins of the present invention, that patent is incorporated by reference herein.

The compounds of formula (I) wherein Z=$CH_2CH_2$ (and the other constituents are as defined above) are believed to be novel. The preferred novel $PGF_{2\alpha}$ derivatives include those novel compounds of formula (I) wherein: X=$CH_2$ and A=$CH_2CH_2$, or cis CH=CH.

The compounds of formula (I) can be prepared by generally employing the methods disclosed in the foregoing references or in the following example. The following synthesis is representative of those which may be used to prepare compounds of the present invention. Those skilled in the art will appreciate the modifications to the synthesis of Example 1 necessary to yield such compounds.

In the foregoing illustrations, as well as those provided hereinafter, a hatched line, as used e.g. at carbon 9, indicates the α configuration. A solid triangular line indicates the β configuration. Dashed lines on bonds indicate a single or double bond. Two solid lines between carbons indicate a double bond of the specified configuration.

In the Example 1 which follows, the following standard abbreviations are used: g=grams (mg=milligrams); mol=moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

EXAMPLE 1

Synthesis of (5Z)-(9S, 11R, 15R)-15-(2-indanyl)-9, 11, 15-trihydroxy-16, 17, 18, 19, 20-pentanor-5-prostenoic acid isopropyl ester (III).

in the presence of 10% Pd/C (50mg) at 40 psi in a Parr hydrogenation apparatus for 1h. The mixture was filtered through Celite 521 and concentrated to afford 2, which was used in the next step without further purification.

B: [3aR, 4R(1E,3R), 5R, 6aS]-4-[3-(2-indanyl)-3-(tetrahydropyran-2-yloxy)propyl]-5-(tetrahydropyran-2-yloxy)-hexahydro-2H-cyclopenta[b]furan-2-one (3)

Compound 2 from above was dissolved in $CH_2Cl_2$ (30mL) and the mixture was cooled to 0° C. 3,4-Dihydro-2H-pyran was added (0.42 g, 5.0 mmol), followed by p-toluenesulfonic acid monohydrate (50mg, 0.2 mmol). The solution was stirred at room temperature for 2h, poured into saturated aqueous $NaHCO_3$, and extracted with $CH_2Cl_2$. The solution was dried over $MgSO_4$, filtered, and concentrated, and the residue was chromatographed on Silica Gel 60 (230–400 mesh ASTM) to afford 0.4 g (36%) of 3 as a viscous oil. $^1$H NMR ($CDCl_3$) δ7.2 (m, 4H), 5.0 (m, 1H), 4.7 (m, 2H), 4.1 (m, 1H), 3.9–3.6 (m, 3H), 3.5 (m, 2H), 3.2–2.5 (bm, 8H), 2.4-2.0 (m, 1H), 1.8–1.3(m, 18H).

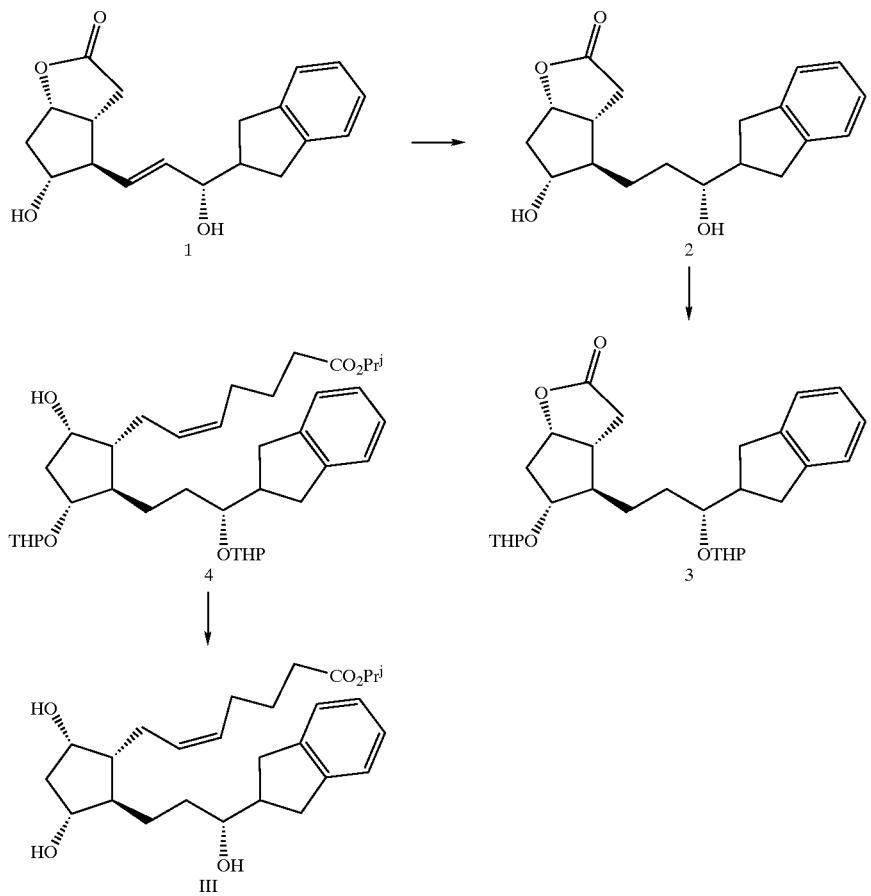

A:[3aR, 4R(1E, 3R), 5R, 6aS]-4-[3-hydroxy-3-(2-indanyl)propyl]-5-hydroxy-hexahydro-2H-cyclopenta[b]furan-2-one (2)

A solution of olefin 1 (0.7g, 2.2 mmol) [synthesis described in: J. Med. Chem. 26:328 (1983)] in 10 mL of a 1:1 v:v mixture of methanol:ethyl acetate was hydrogenated C: (5Z)-(9S, 11R, 15R)-11,15-bis(tetrahydropyran-2-yloxy)-9-hydroxy-15-(2-indanyl)-16,17,18,19,20-pentanor-5-prostenoic acid isopropyl ester (4)

To a −78° C. solution of lactone 3 (0.4 g, 0.8 mmol) in toluene (10 mL) was added a 1.5 M solution of DIBAL-H in hexane (1 mL, 1 mmol). After stirring for 2 h at 0° C., isopropanol (0.2 mL) was added, the mixture was poured into a solution of sodium potassium tartrate, extracted with ethyl acetate (2×50 mL), dried (MgSO$_4$), and concentrated to afford 0.21 g (52%) of crude lactol.

To a solution of (4-carboxybutyl)triphenylphosphonium bromide (0.13 g, 0.3 mmol) in DMSO (6 mL) was added a DMSO solution of sodium methylsulfinylmethide (0.6 mmol, 0.2 M in DMSO). To the mixture was added dropwise a solution of the above lactol (0.15 g, 0.3 mmol) in DMSO (3 mL). The solution was stirred for 16 h at 50° C., cooled to room temperature, and quenched by the addition of 10% aqueous citric acid to pH 5.5. The mixture was extracted with ethyl acetate, dried (MgSO$_4$), filtered, and concentrated.

The crude acid (0.2g, 0.4 mmol) was dissolved in acetone (20 mL) and treated with DBU (0.15 g, 1.0 mmol) and 2-iodopropane (0.17g, 1.0 mmol) for 16h at 23° C., then poured into water and extracted with ether (2×50 mL). The residue was purified by flash chromatography on Silica Gel 60 (230–400 mesh ASTM) with 3:1 hexanes:ethyl acetate to furnish 0.175 g (71%) of the isopropyl ester 4. PMR (CDCl$_3$) δ7.13 (m, 4H), 5.4 (m, 2H), 4.7 (m, 2H), 5.0 (hept, J=6.3 Hz, 1H), 4.8–4.6 (m, 2H), 4.1–3.6 (m, 5H), 3.5(m, 2H), 3.1–2.7 (6m, 4H), 2.3 (t, 2H), 2.1 (m, 2H), 1.9–1.2 (bm, 29H), 1.2 (d, J=6.3 Hz, 6H).

D: (5Z)-(9S,11R,15R)-15-(2-indanyl)-9, 11, 15-trihydroxy-16, 17, 18, 19, 20-pentanor-5-prostenoic acid isopropyl ester (III)

The isopropyl ester, 4, (0.10 g, 0.16 mmol) was dissolved in acetic acid/THF/H$_2$O (4:2:1) and stirred at 50° C. for 30 min., then stirred at 23° C. for 16h. The solution was poured into a saturated aqueous NaHCO$_3$ solution and extracted with ethyl acetate (1×50 mL) and ether (1×50 mL) sequentially. The combined organic extracts were washed with water, dried over MgSO$_4$, filtered and concentrated in-vacuo. The residue was purified by flash chromatography on Silica Gel 60 (230–400 mesh ASTM) with a 3:1 mixture of ethyl acetate:hexanes as element. This yielded 0.017 g (20%) of III as a pale yellow oil. PMR (CDCl$_3$) δ7.1 (m, 4H) 5.4 (m, 2H), 4.9 (hept, J=6.3 Hz, 1H), 4.2 (m,1H), 3.9 (m, 1H), 3.6 (m, 1H), 3.1–2.6 (bm, 5H), 2.3–1.9 (bm, 10H), 1.8–1.3 (bm, 10H), 1.1 (d, J=6.3 Hz, 6H), CMR (CDCl$_3$) δ173.46, 143.01, 142.85, 129.63, 129.33, 126.24, 126.91, 124.47, 124.34, 78.81, 75.26, 74.73, 67.66, 52.91, 52.00, 46.08, 42.59, 35.85, 35.39, 34.25, 34.04, 29.77, 26.90, 26.64, 24.93, 21.84.

The conformationally rigid prostaglandins of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention may be administered as solutions, suspensions, or emulsions (dispersions) in an ophthalmically acceptable vehicle. As used herein, the term "ophthalmically acceptable vehicle" refers to any substance or combination of substances which are effectively non-reactive with the compounds and suitable for administration to a patient. Stabilizers and/or solubilizers are not considered to be reactive substances. Preferred are aqueous vehicles suitable for topical application to the patient's eyes.

The compounds of the present invention are preferably administered topically. The dosage range is generally between about 0.01 and about 1000 micrograms per eye (μg/eye) and is preferably between about 0.1 and 100 μg/eye. In forming compositions for topical administration, the compounds of the present invention are generally formulated as between about 0.001 to about 1.0 percent by weight (wt %) solutions in water at a pH between about 4.5 to 8.0 and preferably between about 7.0 and 7.5. The compounds are preferably formulated as between about 0.0001 to about 0.1 wt % and, most preferably, between about 0.001 and about 0.02 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents and viscosity building agents.

Antimicrobial Preservatives

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; cyclodextrin; CREMOPHORE® EL (polyoxyl 35 castor oil); or other agents known to those skilled in the art. Such co-solvents are typically employed at a level between about 0.01% and about 2% by weight.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight.

The following examples are representative pharmaceutical compositions of the invention for topical use in lowering of intraocular pressure.

EXAMPLE 2

The following formulations A–E are representative pharmaceutical compositions of the invention for topical use in lowering of intraocular pressure. Each of formulations A through E may be formulated in accordance with procedures known to those skilled in the art.

| FORMULATION A | |
|---|---|
| Ingredient | Amount (wt %) |
| Compound of formula II | 0.003 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCl and/or NaOH | pH 7.2–7.5 |
| Purified water | q.s. to 100% |

| FORMULATION B | |
|---|---|
| Ingredient | Amount (wt %) |
| Compound of formula III | 0.001 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.01 |
| Benzalkonium chloride | 0.02 |
| Polysorbate 80 | 0.15 |
| HCl and/or NaOH | pH 7.3–7.4 |
| Purified water | q.s. to 100% |

| FORMULATION C | |
|---|---|
| Ingredient | Amount (wt %) |
| Compound of formula III | 0.001 |
| Dextran 70 | 0.1 |
| Hydroxypropyl methylcellulose | 0.5 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Benzalkonium chloride | 0.01 |
| NaOH and/or HCl | pH 7.3–7.4 |
| Purified water | q.s. to 100% |

| FORMULATION D | |
|---|---|
| Ingredient | Amount (wt %) |
| Compound of formula II | 0.003 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Benzalkonium chloride | 0.01 |
| HCl and/or NaOH | pH 7.3–7.4 |
| Purified water | q.s. to 100% |

| FORMULATION E | |
|---|---|
| Ingredient | Amount (wt/vol %) |
| Compound of formula II | 0.01 |
| Polyoxyl 35 castor oil | 0.1 |
| Tromethamine | 0.12 |
| Boric acid | 0.3 |
| Mannitol | 4.6 |
| Disodium EDTA (edetate disodium) | 0.1 |
| Benzalkonium Chloride Solution | 0.01 |
| HCl and/or NaOH | pH 7.3–7.4 |
| Purified Water | q.s. to 100% |

EXAMPLE 3

In the present study compounds II and III, and $PGF_{2\alpha}$ isopropyl ester ($PGF_{2\alpha}iPr$) were tested for ocular irritation in the New Zealand (NZA) rabbit. Prostaglandins were dosed as 1.0 microgram of compound per treatment in 30 $\mu L$ of test formulation. Conjunctival hyperemia, swelling and discharge were evaluated using a system devised to grossly compare the irritation potential of prostaglandins in the NZA rabbit. Using the Hackett/McDonald scoring system (Hackett, R. B. and McDonald, T. O. "Eye Irritation" in *Dermatotoxicology*, 4th edition, Marzulli, F. N. and Maibach, H. I. editors, Hemisphere Publishing Corp., Washington D.C. (1991)), conjunctival hyperemia, conjunctival swelling, and ocular discharge were graded using a slit-lamp prior to compound instillation and 1, 2, 3, and 5 hours after topical ocular instillation of the test compounds. The percentage of eyes scoring +2 or greater for all time points was calculated for each parameter (conjunctival hyperemia, conjunctival swelling, and ocular discharge). To facilitate comparison, $PGF_{2\alpha}iPr$ was administered at the same time as the test agent. The cumulative results are presented in Table 1.

TABLE 1

| | | % Incidence | | |
|---|---|---|---|---|
| Compound | Number of Animals | Hyperemia | Conjunctival Swelling | Discharge |
| II | 10 | 0 | 0 | 5 |
| $PGF_{2\alpha}$ iPr | 8 | 69 | 59 | 69 |
| III | 10 | 0 | 0 | 0 |
| $PGF_{2\alpha}$ iPr | 10 | 48 | 18 | 13 |

Discussion

It is evident from Table 1 that the conformationally rigid analogs of $PGF_{2\alpha}$ isopropyl ester, compounds II and III, produced a low incidence of ocular irritation in the rabbit compared to $PGF_{2\alpha}$ isopropyl ester, which caused a relatively high incidence of hyperemia, conjunctival swelling and discharge. This indicates that the structural modification present in compounds II and III attenuates the ocular side effects associated with the $PGF_{2\alpha}$ isopropyl ester.

EXAMPLE 4

In the study presented below, compounds II and III, and $PGF_{2\alpha}$ isopropyl ester ($PGF_{2\alpha}$ iPr) were tested for IOP-lowering effect in cynomologus monkey eyes. The right eyes of the cynomologus monkeys in this study were previously given laser trabeculoplasty to induce ocular hypertension in the lasered eye. Animals had been trained to sit in restraint chairs and conditioned to accept experimental procedures without chemical restraint. IOP was determined with a pneumatonometer after light corneal anesthesia with dilute proparacaine. The test protocol included a five-dose b.i.d. treatment regimen because of the typical delayed response to prostaglandins. The test formulations were administered to the lasered right eyes, and the normal left eyes remained untreated for compounds II and III, or to both eyes for $PGF_{2\alpha}$ isopropyl ester ($PGF_{2\alpha}iPr$). Baseline IOP values were determined prior to treatment with the test formulation, and IOP was determined 16 hours after the fourth dose for all compounds, 2, 4, and 6 hours after the fifth dose for compounds II and III, and 1, 3 and 7 hours after the fifth dose for $PGF_{2\alpha}iPr$. Results are presented in Table 2 as the mean percent reduction of IOP from baseline +/− SEM. Prostaglandins were dosed as 1.0 microgram of compound per treatment in 30 μL of test formulation.

TABLE 2

| Compound | Number of Animals | Baseline IOP (mm Hg) | Percent IOP Reduction +/− SEM (Hours after Last Dose/Dose #) | | | | | | |
|---|---|---|---|---|---|---|---|---|---|
| | | | 16/4 | 1/5 | 2/5 | 3/5 | 4/5 | 6/5 | 7/5 |
| II | 9 | 37.9 | 20.9 +/− 4.1 | | 16.3 +/− 5.1 | | 24.2 +/− 5.8 | 27.4 +/− 5.9 | |
| III | 9 | 43.7 | 11.4 +/− 4.0 | | 20.3 +/− 4.6 | | 24 +/− 4.5 | 15 +/− 5.0 | |
| $PGF_{2\alpha}$ iPr | 4 | 34.8 | 5.8 +/− 4.0 | 27.6 +/− 14.4 | | 38 +/− 11.7 | | | 25.6 +/− 14.4 |

Discussion

Table 2 shows that the conformationally rigid analogs of $PGF_{2\alpha}$ isopropyl ester, compounds II and III, produce a significant degree of IOP reduction for the time period tested. Thus, the conformationally rigid compounds II and III, with their low incidence of side effects (Example 3), exhibit a significantly improved therapeutic profile over $PGF_{2\alpha}$ isopropyl ester.

The invention has been described by reference to certain preferred embodiments however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma and ocular hypertension which comprises topically administering to the affected eye a therapeutically effective amount of a compound of formula (I)

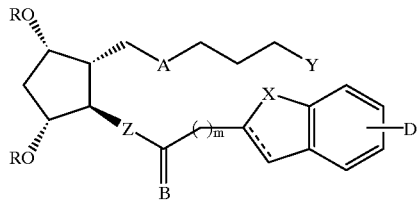

wherein:
$Y=C(O)NR_1R_2$, $CH_2OR_3$, $CH_2NR_1R_2$, $CO_2R_1$, or $CO_2M$, where M is a cationic salt moiety;
$R_1$, $R_2$(same or different)=H, $C_1$–$C_6$ alkyl or alkenyl, or $C_3$–$C_6$ cycloalkyl;
R, $R_3$(same or different)=$C(O)R_4$ or H, where $R_4$=$C_1$–$C_6$ alkyl or alkenyl, or $C_3$–$C_6$ cycloalkyl;
A=$CH_2CH_2$, cis or trans CH=CH, or C≡C;
Z=$CH_2CH_2$ or trans CH=CH;
X=[O, S(O)$_n$, or](CH$_2$)$_n$, where n=0, 1, or 2;
B=H and OH in either configuration or double bonded O;
D=$R_1$, $OR_1$, halogen, S(O)$_n$$R_4$, $NO_2$, $NR_1R_2$, H, or $CF_3$, where n=0, 1, or 2, and $R_1$, $R_2$ and $R_4$ are as defined above; and
m=0, 1, or 2.

2. The method of claim 1, wherein: $Y=CO_2R_1$, where $R_1$=H, $C_1$–$C_6$ alkyl or alkenyl, or $C_3$–$C_6$ cycloalkyl; R=C(O)$R_4$ or H, where $R_4$=$C_1$–$C_6$ alkyl or alkenyl, or $C_3$–$C_6$ cycloalkyl; A=$CH_2CH_2$, cis or trans CH=CH, or C≡C; Z=$CH_2CH_2$ or trans CH=CH; X=[O or] $CH_2$; B=H and OH in either configuration; and D=$R_1$, $OR_1$, halogen, or H, where $R_1$ is as defined above.

3. The method of claim 2, wherein: $Y=CO_2R_1$, where $R_1$=$C_3$ alkyl in the isopropyl form; R=H; A=$CH_2CH_2$ or cis CH=CH; Z=$CH_2CH_2$ or trans CH=CH; X=$CH_2$; B—β=H and α—OH; and D=H.

4. The method of claim 1, wherein between about 0.01 and about 1000 micrograms of the compound is administered.

5. The method of claim 4, wherein between about 0.1 and about 100 micrograms of the compound is administered.

6. A topical ophthalmic composition for the treatment of glaucoma and ocular hypertension, said composition comprising an ophthalmically acceptable vehicle and a therapeutically effective amount of a compound of formula (I):

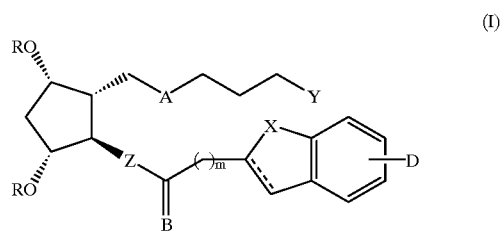

wherein:
$Y=C(O)NR_1R_2$, $CH_2OR_3$, $CH_2NR_1R_2$, $CO_2R_1$, or $CO_2M$, where M is a cationic salt moiety;
$R_1$, $R_2$(same or different)=H, $C_1$–$C_6$ alkyl or alkenyl, or $C_3$–$C_6$ cycloalkyl;
R, $R_3$(same or different)=C(O)$R_4$ or H, where $R_4$=$C_1$–$C_6$ alkyl or alkenyl, or $C_3$–$C_6$ cycloalkyl;
A=$CH_2CH_2$, cis or trans CH=CH, or C≡C;
Z=$CH_2CH_2$, or trans CH=CH;
X=[O, S(O)$_n$, or](CH$_2$)$_n$, where n=0, 1 or 2;
B=H and OH in either configuration or double bonded O;
D=$R_1$, $OR_1$, halogen, S(O)$_n$$R_4$, $NO_2$, $NR_1R_2$, H, or $CF_3$, where n=0, 1, or 2, and $R_1$, $R_2$ and $R_4$ are as defined above; and
m=0, 1, or 2.

7. The composition of claim 6, wherein: $Y=CO_2R_1$, where $R_1$=H, $C_1$–$C_6$ alkyl or alkenyl, or $C_3$–$C_6$ cycloalkyl;

R=C(O)R$_4$ or H, where R$_4$=C$_1$–C$_6$ alkyl or alkenyl, or C$_3$–C$_6$ cycloalkyl; A=CH$_2$CH$_2$, cis or trans CH=CH, or C≡C; Z=CH$_2$CH$_2$, or trans CH=CH; [X=O] X=(CH$_2$)$_n$, where n=1 or 2; B=H and OH in either configuration; and D=R$_1$, OR$_1$, halogen, or H, where R$_1$ is as defined above.

8. The composition of claim 7, wherein: Y=CO$_2$R$_1$, where R$_1$=C$_3$ alkyl in the isopropyl form; R=H; A=CH$_2$CH$_2$ or cis CH=CH; Z=CH$_2$CH$_2$ or trans CH=CH; X=[O or] CH$_2$; β—H and α—OH; and D=H.

9. The composition of claim 8, wherein Z=CH$_2$CH$_2$.

10. The composition of claim 6, wherein the compound is present at a concentration between about 0.0001 and about 5 percent by weight.

11. The composition of claim 9, wherein the compound is present at a concentration between about 0.001 and about 1 percent by weight.

* * * * *